(12) United States Patent
Ganser et al.

(10) Patent No.: US 6,787,301 B2
(45) Date of Patent: Sep. 7, 2004

(54) METHOD AND APPARATUS FOR LASER MICRODISSECTION

(75) Inventors: Michael Ganser, Giessen (DE); Albrecht Weiss, Linden (DE); Joachim Wesner, Frankfurt am Main (DE); Gerhard Johannsen, Wettenberg (DE)

(73) Assignee: Leica Microsystems Wetzlar GmbH, Wetzlar (DE)

( * ) Notice: Subject to any disclaimer, the term of this patent is extended or adjusted under 35 U.S.C. 154(b) by 0 days.

(21) Appl. No.: 09/943,093

(22) Filed: Aug. 31, 2001

(65) Prior Publication Data

US 2002/0056345 A1 May 16, 2002

(30) Foreign Application Priority Data

Sep. 1, 2000 (DE) .......................................... 100 43 506

(51) Int. Cl.⁷ .............................. C12Q 1/00; C12M 1/00
(52) U.S. Cl. ........................ 435/4; 435/283.1; 435/808
(58) Field of Search .......................... 435/4, 283.1, 808

(56) References Cited

U.S. PATENT DOCUMENTS

| 5,843,657 A | * | 12/1998 | Liotta et al. ................... 435/6 |
| 5,859,699 A | * | 1/1999 | Baer et al. .................. 356/246 |
| 5,998,129 A | * | 12/1999 | Schutze et al. ................ 435/4 |
| 6,100,051 A | * | 8/2000 | Goldstein et al. .......... 435/40.5 |
| 6,469,779 B2 | * | 10/2002 | Baer et al. ..................... 356/36 |
| 2002/0048747 A1 | | 4/2002 | Ganser |

* cited by examiner

*Primary Examiner*—Louise N. Leary
(74) *Attorney, Agent, or Firm*—Foley & Lardner LLP

(57) ABSTRACT

A method and an apparatus for laser microdissection of specimen regions (23) of interest of a specimen (4) are described. In a first step, an incomplete cut line (25) enclosing the specimen region (23) of interest is generated by means of a laser beam (7). At the incomplete point of the cut line (25), there remains a web (26) which joins the specimen region (23) of interest to the surrounding specimen (4). In a second step, the web (26) is severed with a single laser pulse directed onto it, thereby completing the cut line. The specimen region (23) of interest is in that context detached from the specimen (4) and falls by the action of gravity into a collection vessel (19).

39 Claims, 3 Drawing Sheets

METHOD AND APPARATUS FOR LASER MICRODISSECTION

CROSS REFERENCE TO RELATED APPLICATIONS

This invention claims priority of the German patent application 100 43 506.8-52 which is incorporated by reference herein.

FIELD OF THE INVENTION

The invention concerns a method and an apparatus for laser microdissection of specimen regions of interest of a specimen that is mounted on a specimen holder.

BACKGROUND OF THE INVENTION

"Microdissection" refers, in the field of biology and medicine, to a method with which a small piece is cut out from a generally flat specimen (for example cells or a tissue section) with a fine, focused laser beam. The cut-out piece is thus available for further biological or medical (e.g. histological) examinations.

U.S. Pat. No. 5,998,129 describes a method of this kind and an apparatus for laser microdissection. The specimen is arranged on a solid, planar support, for example a polymer support film, that is stretched over a glass specimen slide commonly used in laboratories. The method described operates in two steps. In a first step, a specimen region of interest—on which, for example, a selected cell grouping or a histological section is located—is cut out with a laser beam. For that purpose, the cut line of the laser beam describes a complete curve around the specimen region of interest. After cutting, the cut-out specimen region of interest is then still adhering to its substrate or resting on the specimen slide. In a second step, an additional laser shot is therefore directed onto the specimen region of interest, and the specimen region of interest is thereby catapulted in the direction of the laser beam into a collection vessel. Because the cut-out specimen region of interest is catapulted out, the method is therefore referred to in abbreviated fashion among specialists as "laser catapulting."

One disadvantage of the method occurs already in the first method step. Shortly before the cut line is completed, the cut-out sample field is joined to the surrounding specimen only by a narrow web. As a result of electrical charging or mechanical stress in the web, at this stage of the cut the cut-out specimen region of interest often swings away, i.e. out of the focal plane of the laser beam or behind the remaining support film. It thereby becomes difficult or even impossible to complete the cutting of the swung-away, cutout specimen region and to transport it away by a laser shot.

A further disadvantage of the method is the fact that in practice, the laser must be defocused for the second method step (laser-induced transport). This means that in laboratory work, for the removal of each individual cut-out sample field the laser each time must be defocused (e.g. by adjusting the height of the specimen stage supporting the specimen), the individual "transport shot" must be executed, and then the laser must be focused again for further processing of the specimen. For the user, especially in the context of laboratory examinations with a large number of cuts, this procedure is cumbersome and time-consuming.

SUMMARY OF THE INVENTION

It is therefore the object of the invention to describe a method for laser microdissection which allows a specimen field to be cut out from a specimen in reliable and convenient fashion.

This object is achieved by a method for laser microdissection of specimen regions of interest of a specimen that is mounted on a specimen holder which comprises the following method steps:

a) cutting, with a focused laser beam having a defined cut width, along an incomplete cut line largely enclosing the specimen region of interest, such that there remains between the beginning and end of the cut line a stable web of defined width by way of which the specimen region of interest is joined to the surrounding specimen; and b) severing the web with a single laser pulse, directed onto the web, of a focused laser beam having a cut width widened as compared to the previous cutting, such that after severing, the specimen region of interest falls down by the action of gravity.

In the context of this method, it proves advantageous if the defined cut width during cutting is much narrower than the cut width of the laser beam when severing the web. The defined cut width during cutting can be generated by attenuating the laser intensity as compared to the laser intensity when severing the web. In this case a laser pulse at the full power of the laser can be generated to sever the web.

The aperture of the laser beam can also be reduced by means of a stop. The cut width of the laser beam on the specimen is thereby modified. It proves particularly effective if the cut width of the laser beam when severing the web corresponds at least to the width of the web. Advantageously, the single laser pulse is directed onto the center of the web.

It is a further object of the invention to provide an apparatus for laser microdissection which allows a sample field to be reliably cut out of a specimen, and which dispenses with any defocusing of the laser beam to carry off the specimen.

This object is achieved by an apparatus for laser cutting of microscopic specimens which comprises a microscope having at least one objective that defines an optical axis and serves for viewing of a specimen having a specimen region of interest, which furthermore comprises a laser that generates a laser beam, and at least one optical system that couples the laser beam into the objective, and which according to the present invention has the following features:

a) a cut line control unit that is associated with the microscope in order to generate a relative movement between the laser beam and the specimen; and b) means for severing the web, with which the cut width of the laser beam is enlarged and a single focused laser pulse is directed onto the web.

Among specialists it was heretofore generally considered to be impossible to remove a cut-out specimen region of interest from a specimen without laser catapulting. The method according to the present invention now for the first time offers the possibility of cutting out a specimen region of interest and detaching it from the specimen without material-damaging laser bombardment.

For that purpose, laser cutting of the specimen is performed in two method steps with different laser parameters and different laser beam cut widths. Suitable preparation of the specimens is critical for this. For this purpose, the specimens to be examined, from which specimen regions of interest are to be cut out, are prepared on very thin plastic films. The thickness of these plastic films is on the order of between 1 and 2 $\mu$m. PET films, for example, can be used. The best cutting results have been obtained, however, with PEN films. With these it is possible to generate a narrow and at the same time stable web. It has proven particularly favorable for the method if the width of the web corresponds to approximately three to five times the cut width of the laser during cutting. The plastic films are stretched, in known fashion, over a specimen holder. This can be, for example, a glass specimen slide commonly used in laboratories. Other specimen holders (in terms of shape and material) are, however, conceivable. The specimen holder rests on an X-Y stage which allows different specimen regions to be viewed and selected. The apparatus usually has at least one vessel, below or in the vicinity of the specimen, for collecting a cut-out specimen region of interest.

One embodiment of the apparatus according to the present invention has a stationary laser beam. The cut line control unit comprises a displaceable X-Y stage which moves the specimen relative to the stationary laser beam during cutting. In this context, very high demands are made on the positioning accuracy of the X-Y stage in order to produce an exact cut line and a web of suitable width. The X-Y stage is preferably displaced in motorized fashion.

In another embodiment of the apparatus according to the present invention, the cut line control unit comprises a laser scanning device which moves the laser beam relative to a stationary specimen during cutting. For that purpose, the X-Y stage with the specimen holder and specimen on it is not displaced during cutting. The cut line results exclusively from deflection of the laser beam over the specimen.

A particularly advantageous embodiment of the apparatus is one in which a laser control unit which controls the operating parameters of the laser is associated with the laser. Those operating parameters are, for example, the laser power and the laser aperture, which determine the laser cut width. An autofocus apparatus for the laser can additionally be provided; for a clean cut, it ensures reliable focusing even with specimens of different thicknesses.

In another advantageous embodiment, a computer which is used to control the cut line control unit and the laser control unit is associated with the microscope. Automation of the entire method is thereby possible.

In other embodiments of the apparatus, means for selection of the cut line, or means for selection of the cut line and the position of the web by a user, are provided. In addition, means can be provided for selection of the width of the web and for selection of the position of the web by a user. By way of this selection capability, the user can specifically select the correct specimen region of interest before cutting, and at the same time can protect important portions of the specimen from damage. Because the user can, for example, place the cut line on non-critical cell structures of the specimen, cell structures of interest within the specimen region of interest can be protected during cutting.

In a further embodiment, means for automatic enlargement of the cut width of the laser beam and for automatic execution of a single laser pulse, directed onto the web, with that cut width, are associated with the microscope.

The method according to the present invention possesses the advantage of ruling out any swinging away of the specimen region of interest during cutting. Problem-free cutting of the specimen is thereby possible. In addition, severing of the web simultaneously makes possible reliable detachment from the specimen of the cut-out specimen region of interest. The cut-out specimen region of interest then needs only to be collected. Automation of the method and of the apparatus makes possible utilization in routine laboratory operations.

The essential advantage of the method consists, however, in the fact that both cutting and severing of the web are accomplished with a laser beam focused on the cut line and the web, respectively. As a result, the specimen region of interest enclosed by the cut line is protected, during both method steps, from possible damage due to laser irradiation. In this fashion, in contrast to previously known methods, no laser radiation is directed onto the specimen region of interest. This is a very important aspect specifically in the context of biological specimens, since radiation-related changes in cell structures or in genetic information inside the specimen region of interest can in this fashion be ruled out. In addition, it proves advantageous for laboratory operation that the method according to the present invention operates without repeated and therefore time-consuming focusing and defocusing.

BRIEF DESCRIPTION OF THE DRAWINGS

The invention will be described in more detail below with reference to the schematic drawings, in which.

DETAILED DESCRIPTION OF THE INVENTION

Figure 1:
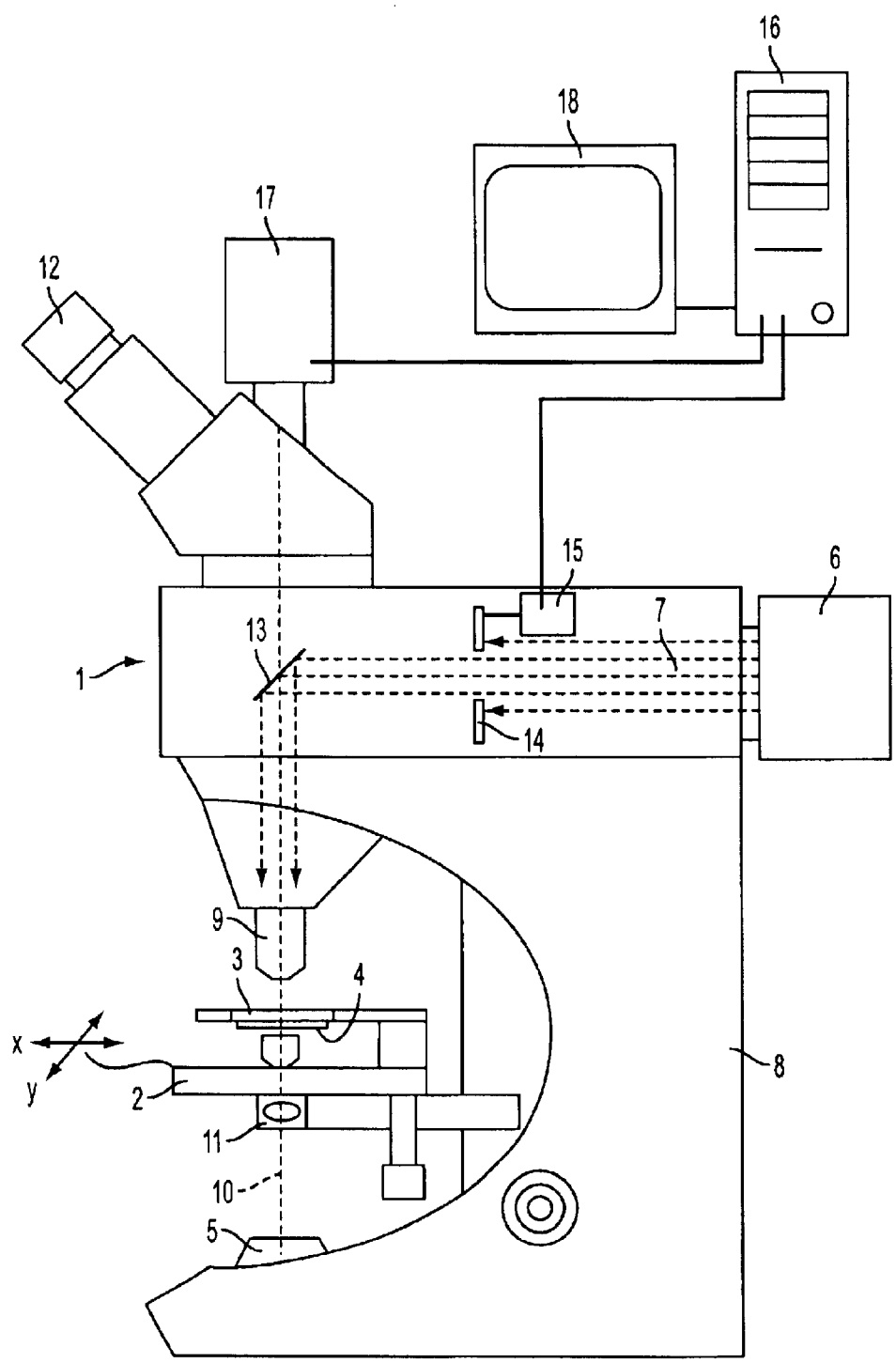
FIG. 1 shows an apparatus for laser cutting with a stationary laser beam.

FIG. 1 depicts an apparatus for laser cutting that operates with a stationary laser beam and a specimen moved relative thereto. It comprises a microscope 1 having an X-Y stage 2 displaceable in motorized fashion. X-Y stage 2 serves to receive a specimen holder 3 on which is mounted a specimen 4 to be examined or cut. Also provided is an illumination system 5, as well as a laser 6 that generates a laser beam 7 which is focused onto specimen 4 in order to cut the latter. X-Y stage 2 serves as a cut line control unit and generates, during the cutting operation, a relative movement between laser beam 7 and specimen 4.

Microscope 1 that is depicted is a transmitted-light microscope, in which illumination system 5 is arranged on a microscope stand 8 below X-Y stage 2 and specimen 4. At least one objective 9 of microscope 1 is arranged above X-Y stage 2 and specimen 4. Objective 9 defines an optical axis 10 that aligns with the optical axis of illumination system 5.

In this arrangement just described, specimen 4 is viewed with transmitted-light illumination. Laser cutting can also be performed with an inverted microscope, in which illumination system 5 is arranged above X-Y stage 2, and the at least one objective 9 is arranged below X-Y stage 2.

The light emitted from illumination system 5 is directed through a condenser 11 from below onto specimen holder 3, with specimen 4, arranged on X-Y stage 2. The light penetrating through specimen 4 arrives at objective 9 of microscope 1. Within microscope 1 the light is conveyed via lenses and mirrors (not depicted) to at least one eyepiece 12 of microscope 1, through which an operator can view specimen 4 arranged on X-Y stage 2.

In microscope stand 8 of microscope 1, an optical system 13 is provided in optical axis 10 of objective 9. Optical system 13 can be, for example, a dichroic splitter. It is furthermore conceivable for optical system 13 to comprise multiple optical components. Such is the case when laser beam 7 needs to be deflected several times. A stop 14, with which the diameter of laser beam 7 can be limited in appropriate fashion, is also provided in laser beam 7. Stop 14 can be configured, for example, as a fixed stop. In an advantageous embodiment, multiple fixed stops 14 can be arranged on a revolving disk or on a linear slider, so that one of these fixed stops can be introduced into the beam path as the particular requisite stop 14. Introduction into laser beam 7 can be performed manually by the user, or in motorized fashion.

In the embodiment depicted here, stop 14 is configured as a variable stop, for example as an iris diaphragm whose diameter is controlled via a diaphragm motor 15. Diaphragm motor 15 receives from a computer 16 the necessary control signals for setting the requisite diaphragm diameter.

Microscope 1 is furthermore equipped with a camera 17 which acquires an image of specimen 4 that is to be cut. This image can be displayed on a monitor 18 that is connected to computer 16. The system made up of computer 16, camera 17, and monitor 18 can be used to observe and monitor the cutting operation performed with laser 4. For example, the computer can deliver trigger signals to the laser to initiate laser pulses and to control laser power, can activate diaphragm motor 15, and can activate an autofocus device (not depicted) for laser 6.

In addition, the specimen region of interest of specimen 12 that is to be cut out can be traced around on monitor 18 using a mouse cursor. The position of the web can be determined automatically by a software program in computer 16. It proves to be advantageous, however, if a user can also predetermine the position of the web by means of a mouse click. Along the cut line thereby characterized, the cutting operation by means of laser 4 is then performed.

Arranged below specimen 4 is at least one collection vessel 19 for collecting the cut-out specimen region of interest.

Figure 2:
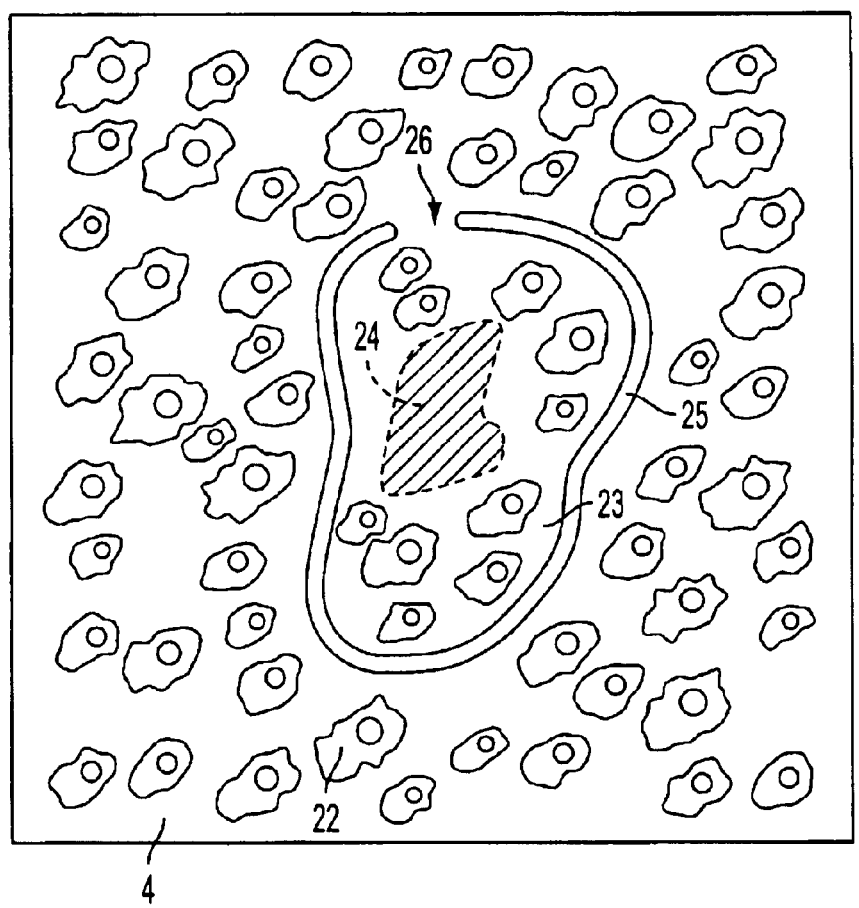
FIG. 2 shows a specimen with a cut profile according to the present invention around a specimen region of interest.

The method according to the present invention will be described below with reference to FIG. 2.

The Figure depicts a camera image of a specimen 4 having a plurality of cells 22. Located approximately in the center of specimen 4 is a specimen region 23 of interest in which an atypical cell structure 24, e.g. a suspected cancer cell or a cell with a genetic code of interest, is located. This specimen region 23 of interest is to be removed from specimen 4 for further examination.

For that purpose, a desired reference cut line for the cutting operation that is to be performed is marked by a user in the camera image, using a corresponding software program, by means of a computer mouse. In addition, the desired position of the web is marked. The width of the web can be defined by the user. The possibility also exists, however, of allowing the web width to be identified by computer 16 as a function of the present laser parameters.

Corresponding to the presently set cut width of laser beam 7, a number of reference positions of laser beam 7 on specimen 4 for the defined reference cut line is calculated by computer 16, the successively arranged reference positions of laser beam 7 resulting in the desired reference cut line. For the defined web exclusively, only one central reference position is calculated.

To prepare for the cutting operation, a narrow cut width of laser beam 7 is then set. During cutting, X-Y stage 2 is then displaced in steps in such a way that laser beam 7 successively strikes the calculated reference position(s) on specimen 4, the reference position for web 26 initially being omitted. In each reference position, a respective trigger signal is generated by computer 16 and sent to laser 6, and a laser pulse is correspondingly emitted by it. In this fashion, the discontinuous cut line 25 that is depicted is generated with laser 6 around specimen region 23 of interest. Specimen region 23 of interest is then joined to the surrounding specimen 4 only by the stable web 26.

To prepare for the severing of web 26, the cut width of laser beam 7 is then considerably widened. It can be set, for example, to the maximum possible cut width. It has proven advantageous, however, if the cut width for severing web 26 is adapted to the width of web 26. For that purpose, the cut width must correspond at least to the width of web 26.

In the last method step, said web 26 is severed with a laser pulse directed onto its center. This is a cutting operation with a single laser pulse, in which context laser 6 remains focused in the same way as during the previous cutting of cut line 25. Specimen region 23 of interest that is dissected in this fashion falls down into a collection vessel arranged below it.

Since both the cutting of cut line 25 and the severing of web 26 are accomplished with a focused laser beam 7, specimen region 23 of interest is protected, during both method steps, from possible damage due to laser irradiation.

Figure 3:
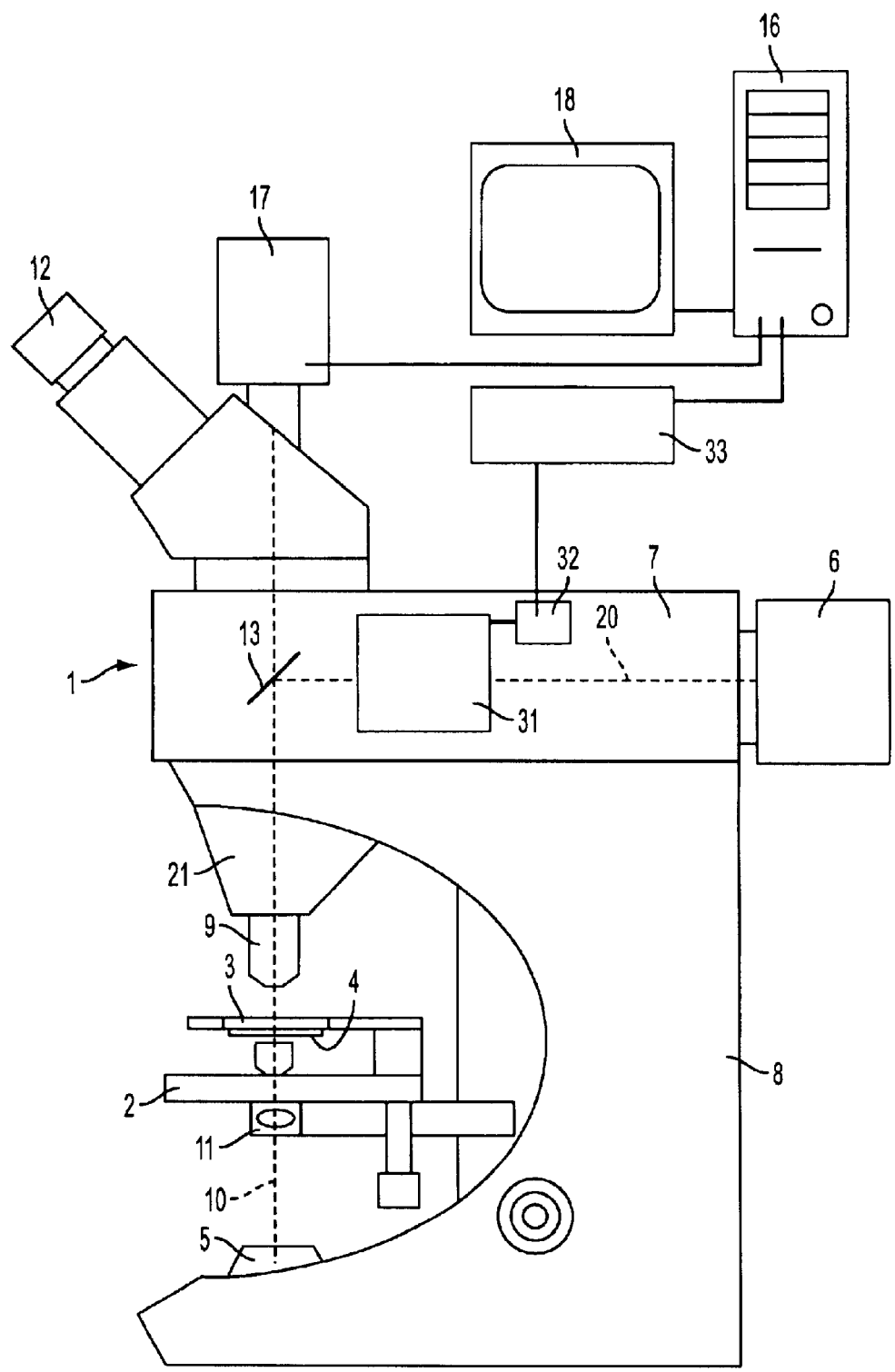
FIG. 3 shows an apparatus for laser cutting with a movable laser beam.

FIG. 3 shows a laser microdissection unit according to the present invention for carrying out the method according to the present invention, which moves a laser beam over a stationary specimen during cutting.

The laser microdissection unit comprises a microscope 1 having a displaceable X-Y stage 2 on which a specimen holder 3 is arranged. Located on the underside of specimen holder 3 is a specimen 4 to be cut. Arranged below X-Y stage 2 are an illumination system 5 and a condenser 11 which illuminates specimen 4. During the cutting operation, X-Y stage 2 is not moved horizontally, i.e. in the X and Y directions. At least one collection vessel 19, for collecting the cut-out specimen region of interest, is arranged below specimen 4.

A laser beam 7 proceeds from a laser 6 (in this example, a UV laser) and is coupled into an illuminating beam path 20. A laser scanning device 31 is arranged in illuminating beam path 20. Laser beam 7 passes through laser scanning device 31 and arrives via an optical system 13 at an objective 9 which focuses laser beam 7 on specimen 4. Optical system 13 is advantageously embodied as a dichroic splitter, through which an imaging beam path 21 proceeding from specimen 4 through objective 9 arrives at at least one eyepiece 12.

In this embodiment, the adjustment of laser scanning device 31 and therefore the displacement of laser beam 7 on specimen 4 are accomplished with a motor 32 associated with laser scanning device 31, a control unit 33, and a computer 16. Motor 32 is connected to control unit 33, which supplies the control signals for activation of motor 32. Control unit 33 is connected to computer 16, to which a monitor 18 is connected. The image of specimen 4 acquired by a camera 17 is displayed on monitor 18. A desired reference cut line can be defined on monitor 18 in the camera image by means of a computer mouse (not depicted) or any other cursor control device. Computer 16 is furthermore connected to laser light source 6, and delivers trigger signals to it to initiate laser pulses only when a cut is being performed.

Laser scanning device 31 itself serves as a cut line control unit that generates, during the cutting operation, a relative movement between laser beam 7 and specimen 4. Focusing of laser beam 7 can be accomplished by a user by manually moving X-Y stage 2 vertically while simultaneously visually monitoring the camera image. An embodiment of the apparatus that comprises an autofocus apparatus (not depicted) for laser beam 7 is, however, more user-friendly.

Activation of laser scanning device 31 causes laser beam 7 to appear at the output of laser scanning device 31 at various deflection angles. By varying the deflection angle, laser beam 7 can be guided to any desired positions on specimen 4 that lie within the field of view of objective 10.

In the first method step, by suitable activation of laser scanning device 31 an incomplete cut line is generated on specimen 4 with a laser beam 7 having a small cut width, a stable web 26 remaining behind. For that purpose, the narrow cut width must already be set previously.

The cut width of a laser in a specimen depends on the laser parameters, for example the laser power and the aperture of laser beam 7. This cut width is determined previously or is stored in a table in computer 16 as a function of the laser parameters. Corresponding to the presently set cut width, for the defined reference cut line a number of reference positions of the laser beam on specimen 4 is calculated, the successively arranged reference positions of laser beam 7 resulting in the desired reference cut line.

The reference positions on specimen 4 are then moved to in succession with laser scanning device 31. Each time the reference position of laser beam 7 on specimen has been prepared or set by means of laser scanning device 31, computer 16 supplies trigger signals to initiate laser pulses at laser light source 6. In this fashion, the incomplete cut line is generated in steps, a stable web remaining behind.

As preparation for severing the web, the cut width of laser beam 7 is then set much wider. It should, however, correspond at least to the width of the web. Laser beam 7 remains focused in this second method step as well. Only a single laser pulse is generated in order to sever the web, the briefly generated laser beam 7 preferably being directed onto the center of the web.

After the web has been severed, the specimen region of interest is completely detached from specimen 4 and falls, by the action of gravity, into the collection vessel arranged beneath it.

The present invention was described with reference to exemplary embodiments. It is nevertheless apparent to any person skilled in this art that changes and modifications can be made without thereby leaving the range of protection of the claims recited hereinafter.

PARTS LIST

1 Microscope
2 Displaceable X-Y stage
3 Specimen holder
4 Specimen
5 Illumination system
6 Laser
7 Laser beam
8 Microscope stand
9 Objective
10 Optical axis
11 Condenser
12 Eyepiece
13 Optical system
14 Stop
15 Stop motor
16 Computer
17 Camera
18 Monitor
19 Collection vessel
20 Illuminating beam path
21 Imaging beam path
22 Cells
23 Specimen region of interest
24 Atypical cell structure
25 Cut line
26 Web
31 Laser scanning device
32 Motor for laser scanning device
33 Control unit

What is claimed is:

1. A method for laser microdissection of specimen regions of interest of a specimen that is mounted on a specimen holder, comprising:

a) cutting, with a focused laser beam having a defined cut width, along an incomplete cut line largely enclosing the specimen region of interest, such that there remains between a beginning and end of the cut line a stable web of defined width by way of which the specimen region of interest is joined to the surrounding specimen; and b) severing the web with a laser pulse, directed onto the web, of a focused laser beam having an enlarged cut width enlarged as compared to said defined cut width.

2. The method as defined in claim 1, wherein the defined cut width during cutting is much narrower than the enlarged cut width.

3. The method as defined in claim 1, wherein the defined cut width during cutting is generated by attenuating a laser intensity as compared to a laser intensity when severing the web.

4. The method as defined in claim 1, wherein the enlarged cut width corresponds at least to a width of the web.

5. The method as defined in claim 1, wherein the laser pulse is directed onto the center of the web.

6. An apparatus for laser cutting of microscopic specimens, comprising:

a microscope configured for viewing of a specimen having a specimen region of interest, comprising: at least one objective that defines an optical axis; a laser that generates a laser beam; and at least one optical system that couples the laser beam into the objective, wherein a) a cut line control unit is associated with the microscope and configured to generate a relative movement between the laser beam and the specimen to achieve an incomplete cut line largely enclosing the specimen region of interest, such that there remains between a beginning and end of the cut line a stable web of defined width by way of which the specimen region of interest is joined to the surrounding specimen; and b) means for severing the web, with which a cut width of the laser beam is enlarged and a single focused laser pulse is directed onto the web and severs the web, are provided.

7. The apparatus as defined in claim 6, wherein the laser beam is stationary and the cut line control unit comprises a displaceable X-Y stage which moves the specimen relative to the stationary laser beam during cutting.

8. The apparatus as defined in claim 6, wherein the cut line control unit comprises a laser scanning device which moves the laser beam relative to a stationary specimen during cutting.

9. The apparatus as defined in claim 6, wherein a laser control unit which controls operating parameters of the laser is associated with the laser.

10. The apparatus as defined in claim 6, wherein an autofocus apparatus for the laser beam is associated with the laser.

11. The apparatus as defined in claim 9, wherein a computer for controlling the cut line control unit and the laser control unit is associated with the microscope.

12. The apparatus as defined in claim 6, wherein means for automatic enlargement of the cut width of the laser beam and for automatic execution of a single laser pulse, directed onto the web, with that cut width, are associated with the microscope.

13. The apparatus as defined in claim 6, wherein means for selection of the cut line by a user are provided.

14. The apparatus as defined in claim 6, wherein means for selection of the defined width of the web by a user are provided.

15. The apparatus as defined in claim 6, wherein means for selection of the location of the web by a user are provided.

16. A method for laser microdissection of a specimen region of interest of a specimen, comprising:

(a) cutting with a laser beam along an incomplete cut line such that there remains a stable web by way of which the specimen region of interest is joined to the surrounding specimen; and (b) severing the web with a laser pulse, directed onto the web, of a laser beam.

17. A method as set forth in claim 16, wherein step (b) comprises severing the web with a single laser pulse.

18. A method as set forth in claim 16, wherein step (a) comprises cutting with a focused laser beam and step (b) comprises severing the web with a laser pulse of a focused laser beam.

19. A method as set forth in claim 16, wherein step (b) comprises severing the web with a laser pulse of a laser beam having a cut width enlarged as compared to step (a).

20. A method as set forth in claim 16, wherein in step (a) there remains only one stable web.

21. A method as set forth in claim 20, wherein the only one stable web remains between the beginning and end of a cut line.

22. A method as set forth in claim 16, wherein the incomplete cut line largely encloses the specimen region of interest.

23. A computer readable storage medium containing instructions to perform the method of claim 16.

24. An apparatus for laser cutting of microscopic specimens comprising:

a microscope having at least one objective that defines an optical axis, for viewing of a specimen having a specimen region of interest;

a laser that generates a laser beam and at least one optical system that couples the laser beam into the objective; and a control unit associated with the microscope which generates a relative movement between the laser beam and the specimen to achieve an incomplete cut line such that there remains a stable web by way of which the specimen region of interest is joined to the surrounding specimen, and to sever the web with a laser pulse directed onto the web.

25. An apparatus as set forth in claim 24, wherein the control unit severs the web with a single laser pulse.

26. An apparatus as set forth in claim 24, wherein the incomplete cut line is formed by a focused laser beam and the web is severed using a focused laser beam.

27. An apparatus as set forth in claim 24, wherein the web is severed with a laser pulse of a laser beam having a cut width enlarged as compared to a cut width used to achieve the incomplete cut line.

28. An apparatus as set forth in claim 24, wherein after the incomplete cut line is achieved there remains only one stable web.

29. An apparatus as set forth in claim 28, wherein the only one stable web remains between the beginning and end of a cut line.

30. An apparatus as set forth in claim 24, wherein the incomplete cut line largely encloses the specimen region of interest.

31. An apparatus as set forth in claim 24, wherein the microscope comprises an upright microscope.

32. An apparatus as set forth in claim 24, wherein the microscope comprises an inverted microscope.

33. An apparatus as set forth in claim 24, wherein the apparatus further comprises a displaceable X-Y stage.

34. An apparatus as set forth in claim 24, wherein the apparatus further comprises a laser scanning device.

35. An apparatus as set forth in claim 24, further comprising an autofocus apparatus.

36. An apparatus as set forth in claim 24, further comprising an input unit to receive an instruction from a user which designates the cut line.

37. An apparatus as set forth in claim 24, further comprising an input unit to receive an instruction from a user which designates a width of the web.

38. An apparatus as set forth in claim 24, further comprising an input unit to receive an instruction from a user which designates a location of the web.

39. The method as defined in claim 1, wherein step b) comprises severing the web with a single laser pulse.

* * * * *